(12) United States Patent
Montpetit et al.

(10) Patent No.: US 8,979,732 B2
(45) Date of Patent: *Mar. 17, 2015

(54) METHOD AND APPARATUS FOR TREATMENT OF VAGINAL ANTERIOR REPAIRS

(75) Inventors: Karen Pilney Montpetit, Mendota Heights, MN (US); Matthew J. Olson, Crystal, MN (US)

(73) Assignee: AMS Research Corporation, Minnetonka, MN (US)

( * ) Notice: Subject to any disclaimer, the term of this patent is extended or adjusted under 35 U.S.C. 154(b) by 269 days.

This patent is subject to a terminal disclaimer.

(21) Appl. No.: 13/247,565

(22) Filed: Sep. 28, 2011

(65) Prior Publication Data

US 2012/0065462 A1 Mar. 15, 2012

Related U.S. Application Data

(60) Division of application No. 11/463,654, filed on Aug. 10, 2006, now Pat. No. 8,062,206, which is a continuation-in-part of application No. 10/840,646, filed on May 7, 2004, now Pat. No. 7,351,197.

(51) Int. Cl.
*A61F 2/00* (2006.01)
*A61B 17/06* (2006.01)
*A61B 19/02* (2006.01)
*A61B 17/00* (2006.01)

(52) U.S. Cl.
CPC ......... *A61F 2/0045* (2013.01); *A61B 17/06109* (2013.01); *A61B 19/026* (2013.01); *A61B 2017/00805* (2013.01); *A61B 2017/06076* (2013.01)

USPC .......................................................... 600/30

(58) Field of Classification Search
USPC ............................................. 600/29, 30, 37
See application file for complete search history.

(56) References Cited

U.S. PATENT DOCUMENTS

| | | |
|---|---|---|
| 5,112,344 A | 5/1992 | Petros |
| 5,611,515 A | 3/1997 | Benderev et al. |
| 5,842,478 A | 12/1998 | Benderev et al. |
| 5,860,425 A | 1/1999 | Benderev et al. |
| 5,899,909 A | 5/1999 | Claren et al. |
| 6,039,686 A | 3/2000 | Kovac |
| 6,042,534 A | 3/2000 | Gellman et al. |
| 6,080,116 A | 6/2000 | Erickson et al. |

(Continued)

FOREIGN PATENT DOCUMENTS

| | | |
|---|---|---|
| EP | 0854691 | 3/1996 |
| WO | WO 97/13465 | 4/1997 |

(Continued)

OTHER PUBLICATIONS

American Medical Systems, Monarc™ Subfascial Hammock, 2003.

(Continued)

*Primary Examiner* — John Lacyk
(74) *Attorney, Agent, or Firm* — Kagan Binder, PLLC

(57) ABSTRACT

An apparatus for repairing cystocele including an adjustable support member, a pair of superior support arms continuously knitted with said support member, and a pair of inferior support arms continuously knitted with said support member, wherein the distance between the pair of superior support arms and pair of inferior support arms can be increased or decreased by modifying the shape of the support member.

7 Claims, 25 Drawing Sheets

(56) References Cited

U.S. PATENT DOCUMENTS

| | | | |
|---|---|---|---|
| 6,110,101 A | 8/2000 | Tihon et al. |
| 6,273,852 B1 | 8/2001 | Lehe et al. |
| 6,478,727 B2 | 11/2002 | Scetbon |
| 6,612,977 B2 | 9/2003 | Staskin et al. |
| 6,638,211 B2 | 10/2003 | Suslian et al. |
| 6,641,525 B2 | 11/2003 | Rocheleau et al. |
| 6,908,425 B2 | 6/2005 | Luscombe |
| 6,911,003 B2 | 6/2005 | Anderson et al. |
| 6,932,759 B2 | 8/2005 | Kammerer et al. |
| 6,960,160 B2 | 11/2005 | Browning |
| 6,991,597 B2 | 1/2006 | Gellman et al. |
| 7,037,255 B2 | 5/2006 | Inman et al. |
| 7,083,568 B2 | 8/2006 | Neisz et al. |
| 7,112,171 B2 | 9/2006 | Rocheleau et al. |
| 7,131,943 B2 | 11/2006 | Kammerer |
| 7,351,197 B2* | 4/2008 | Montpetit et al. | 600/30 |
| 2002/0007222 A1 | 1/2002 | Desai |
| 2002/0077526 A1 | 6/2002 | Kammerer et al. |
| 2002/0099258 A1 | 7/2002 | Staskin et al. |
| 2002/0147382 A1 | 10/2002 | Neisz et al. |
| 2002/0156489 A1 | 10/2002 | Gellman et al. |
| 2002/0188169 A1 | 12/2002 | Kammerer et al. |
| 2003/0023137 A1* | 1/2003 | Gellman | 600/30 |
| 2003/0032929 A1 | 2/2003 | McGuckin |
| 2003/0130670 A1 | 7/2003 | Anderson et al. |
| 2003/0171644 A1 | 9/2003 | Anderson et al. |
| 2003/0176762 A1 | 9/2003 | Kammerer |
| 2003/0176875 A1 | 9/2003 | Anderson et al. |
| 2003/0233108 A1 | 12/2003 | Gellman et al. |
| 2004/0006353 A1 | 1/2004 | Bosley, Jr. et al. |
| 2004/0039453 A1 | 2/2004 | Anderson et al. |
| 2004/0087970 A1 | 5/2004 | Chu et al. |
| 2004/0225181 A1 | 11/2004 | Chu et al. |
| 2004/0230206 A1 | 11/2004 | Gellman et al. |
| 2004/0230207 A1 | 11/2004 | Gellman et al. |
| 2005/0037132 A1 | 2/2005 | Horres et al. |
| 2005/0075660 A1 | 4/2005 | Chu et al. |
| 2005/0080317 A1 | 4/2005 | Merade |
| 2005/0131393 A1 | 6/2005 | Chu et al. |
| 2005/0143618 A1 | 6/2005 | Anderson et al. |
| 2005/0245787 A1 | 11/2005 | Cox et al. |
| 2005/0250977 A1 | 11/2005 | Montpetit et al. |
| 2006/0041185 A1 | 2/2006 | Browning |
| 2006/0058574 A1 | 3/2006 | Priewe et al. |
| 2006/0058578 A1 | 3/2006 | Browning |
| 2006/0089524 A1 | 4/2006 | Chu |
| 2006/0089525 A1 | 4/2006 | Mamo et al. |
| 2006/0122457 A1 | 6/2006 | Kovac et al. |
| 2006/0141861 A1 | 6/2006 | Darley et al. |
| 2006/0195011 A1 | 8/2006 | Arnal et al. |
| 2006/0229493 A1 | 10/2006 | Weiser et al. |
| 2006/0260618 A1 | 11/2006 | Hodroff et al. |
| 2007/0015953 A1 | 1/2007 | MacLean |

FOREIGN PATENT DOCUMENTS

| | | |
|---|---|---|
| WO | WO 99/59477 | 11/1999 |
| WO | WO 01/89440 | 11/2001 |
| WO | WO 02/39890 | 5/2002 |
| WO | WO 02/069781 | 9/2002 |
| WO | WO 03/013392 | 2/2003 |
| WO | 03096929 A1 | 11/2003 |
| WO | WO 2005/037132 | 4/2005 |
| WO | 2005110274 A2 | 11/2005 |
| WO | WO 2005/107606 | 11/2005 |
| WO | WO 2006/041861 | 4/2006 |

OTHER PUBLICATIONS

American Medical Systems website, SPARC Sling System—A Superior Approach to Tensionless Sling Placements, 2001.
American Medical Systems website, SPARC Sling System Procedure Guide, 2002.

* cited by examiner

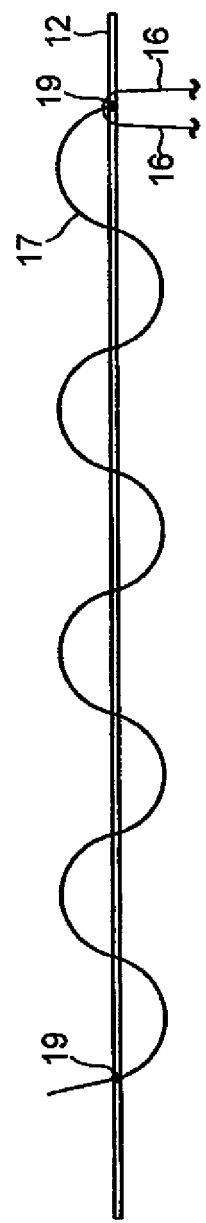

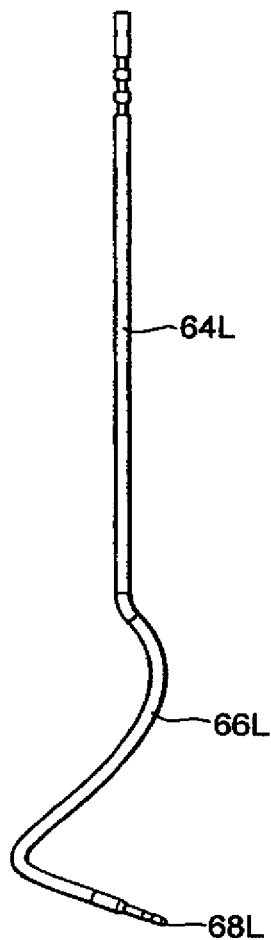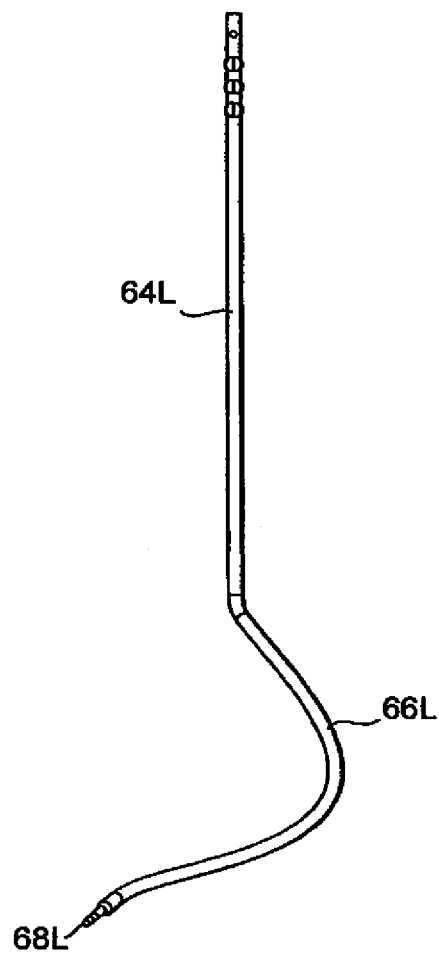
Fig. 19        Fig. 20
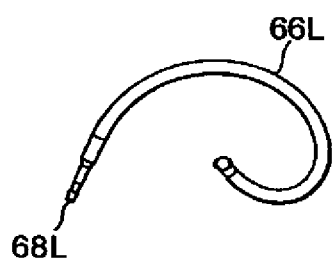
Fig. 21

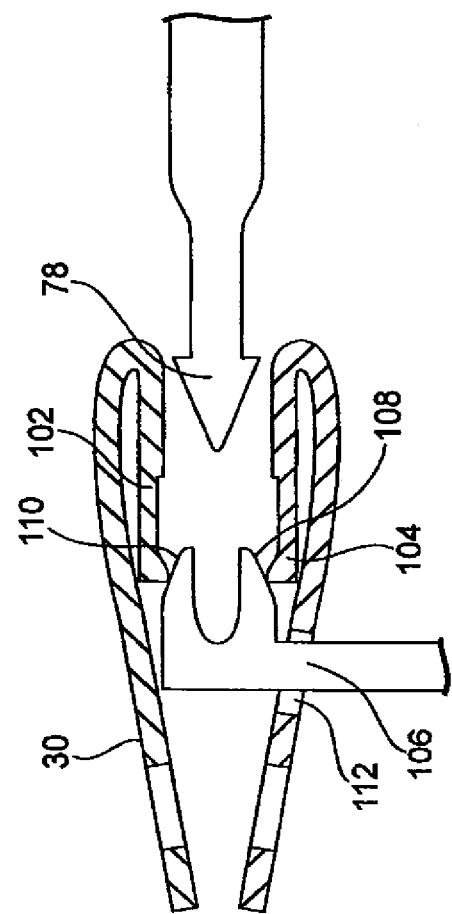

METHOD AND APPARATUS FOR TREATMENT OF VAGINAL ANTERIOR REPAIRS

CROSS REFERENCE TO RELATED APPLICATIONS

The present application is a divisional of U.S. patent application Ser. No. 11/463,654, filed Aug. 10, 2006now U.S. Pat. No. 8,062,206, entitled "Method and Apparatus for Treatment of Vaginal Anterior Repairs," which is a continuation-in-part of U.S. patent application Ser. No. 10/840,646, filed May 7, 2004, (now U.S. Pat. No. 7,351,197), entitled "Method and Apparatus for Cystocele Repair" All of the aforementioned applications are hereby incorporated by reference in their entireties.

FIELD OF THE INVENTION

This invention relates generally to the field of urogenital surgery. More specifically, this invention relates to the treatment of vaginal or vault prolapse and to a device suitable for use in such treatment.

BACKGROUND OF THE INVENTION

Vault or vaginal prolapse develops when intra-abdominal pressure pushes the vagina outside the body. This condition develops when the utero-sacral ligaments, which hold the vagina in position within the body cavity, are severed or damaged. The result of such damage is that the vagina has a tendency to invert which is uncomfortable and unhealthy, and renders the vagina unsuitable for intercourse.

Many techniques have been tried to correct or ameliorate the prolapse and its symptoms, with varying degrees of success. Nonsurgical treatment of prolapse involves measures to improve the factors associated with prolapse, including treating chronic cough, obesity, and constipation. Other nonsurgical treatments may include pelvic muscle exercises or supplementation with estrogen. These therapies may alleviate symptoms and prevent worsening, but the actual hernia will remain. Vaginal pessaries are the primary type of nonsurgical treatment, but there can be complications due to vaginal wall ulceration.

There is a desire to obtain a minimally invasive yet highly effective device and method that can be used to treat pelvic organ prolapse with minimal to no side effects. Such a device should reduce the complexity of the surgical procedure, be biocompatible, adjustable, and non-toxic. The treatment methods using the device should reduce pain, operative risks, infections and post operative hospital stays. Further, the method of treatment should also improve the quality of life for patients.

SUMMARY OF THE INVENTION

The invention includes a method and apparatus for cystocele repair. In one embodiment, the method includes the steps of: establishing four pathways in tissue around a bladder of a patient, introducing an attachment arm into each of the pathways, and positioning a support member beneath the bladder of the patient. The support member is configured to allow for a variable attachment-arm position, wherein the support member has each of the attachment arms connected thereto such that the bladder of the patient is supported by the support member. A bulge of the bladder into a vagina of the patient is reduced as a consequence of applying this method.

In another embodiment, an apparatus for repairing cystocele includes a support surface knitted with a pair of superior attachment arms, and a pair of inferior attachment arms, wherein the distance between the pair of superior attachment arms and the pair of inferior attachment arms can be increased or decreased.

In another embodiment, the invention includes a kit for repairing cystocele. The kit includes a support apparatus including a pair of superior attachment arms and a pair of inferior attachment arms. Each of the attachment arms includes a connector configured to removably mate with a tip of a needle. The kit further includes a first needle configured to extend from an incision on the left side of the patient where a left inferior edge of the pubic ramus bone of the patient ends at the bottom of the left obturator foramen of the patient, through the left obturator foramen of the patient, to an incision in the vagina of the patient; and a second needle configured to extend from an incision on the right side of the patient where a right inferior edge of the pubic ramus bone of the patient ends at the bottom of the right obturator foramen of the patient, through the right obturator foramen of the patient, to the incision in the vagina of the patient.

In another embodiment, a surgical implant kit includes an adjustable support apparatus including at least two pairs of attachment arms, each of the attachment arms comprises a connector configured to removably mate with a tip of a needle. Each connector has an aperture configured to receive the tip of the needle. Each aperture has a different shape. The kit further includes at least two needles, each needle having a tip having a shape configured to removably mate with one aperture of the at least two connectors.

In another embodiment, a surgical implant kit includes an adjustable support apparatus including at least two pairs attachment arms, wherein the distance between the respective pairs of attachment arms is adjustable. Each of the attachment arms includes a connector configured to mate with a tip of a needle, wherein the connector is capable of being subsequently removed and reattached to the needle. Each connector has identifying indicia thereon. The kit further includes at least two needles.

In yet another embodiment, the invention includes a surgical implant kit including an adjustable support apparatus having at least two pairs of attachment arms. Each of the attachment arms includes a connector configured to removably mate with a tip of a needle. The kit further includes at least four needles, each needle having a handle and each handle having a color matching a color of a corresponding connector.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 3 is a side view of an attachment arm of a variable attachment arm support apparatus of the present invention;

FIG. 4 is a top view of an attachment arm of a variable attachment arm support apparatus of the present invention;

FIG. 19 is a right side view of an embodiment of a left inferior needle shaft of the present invention, without a handle;

FIG. 20 is a bottom view of an embodiment of the left inferior needle shaft of the present invention, without a handle;

FIG. 21 is a front view of an embodiment of the left inferior needle shaft of the present invention, without a handle;

FIG. 34 is a top cross-sectional view of a removal tool disengaging a connector from a needle tip during a second phase.

DETAILED DESCRIPTION OF THE PREFERRED EMBODIMENTS

Figure 1:
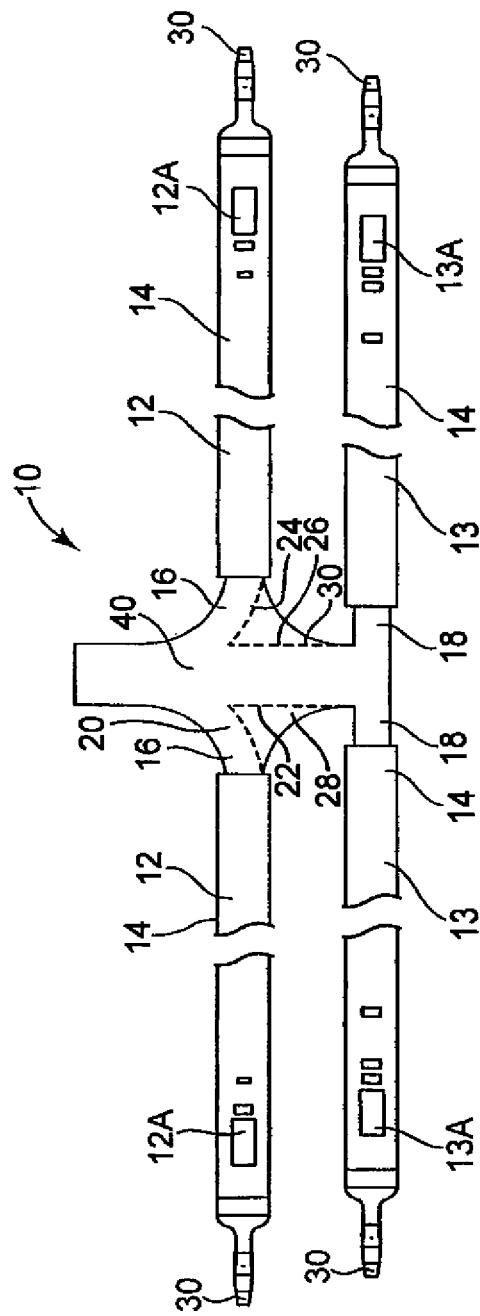
FIG. 1 is a fragmentary top view of a variable attachment arm support apparatus.

Referring now to the drawings, wherein like reference numerals designate identical or corresponding parts throughout the several views, FIG. 1 illustrates a variable attachment surgical support apparatus 10 of the present invention. The apparatus 10 is configured to be surgically implanted in a female patient to repair anterior prolapse of the vagina. The present invention may be used to correct central defects, midline defects, or both midline and central defects at once. In the embodiment shown in FIG. 1, apparatus 10 comprises two superior attachment arms 12, two inferior attachment arms 13, and a support member 40. Each of attachment arms 12 and 13 include a connector 30. Each attachment arm 12 and 13 is covered by a sheath 14. Attachment arms 12 and 13 are connected to support member 40 by known means.

Sheath 14 is preferably of fabricated of polyethylene, although a variety of materials, such as polypropylene, nylon, polyester, or Teflon™ may be used while remaining within the scope of the invention. The sheath is configured to be removed from the attachment arm after the attachment arm is in the desired position in the body.

Attachment arms 12 and 13 are preferably about 19 inches long and about 0.433 inches wide. The attachment arms 12 and 13 are about 0.024 inches thick. Attachment arms 12 and 13 are fabricated of a knit 4 or 6 mil polypropylene monofilament and are heat set at about 280-300 degrees Fahrenheit for 5-8 minutes. Also, in one embodiment, support member 40 is about 10 cm long by about 5 cm wide and about 0.021 inches thick. Member 40 is knitted of 4 mil polypropylene monofilament and heat set at about 310-330 degrees Fahrenheit for about 5-8 minutes. Both the attachment arm and support member have a stitch count of 27.5 courses/inch (±2 courses) and 13 wales/inch (±2 wales).

In another embodiment, the attachment arms are knitted with bar settings of: Bar 1: 1/0, 2/1 and Bar 2: 0/1, 1/2. The support member is a large pore mesh, knitted with bar settings of: Bar 1: 1/0, 2/3, 2/1, 2/3, 1/0, 1/2, 1/0, 1/2; Bar 2: 1/0, 2/3, 2/3, 1/0; and Bar 3: 2/3, 1/0, 112, 1/0, 2/3, 2/1, 2/3, 2/1. The attachment arms are connected to the support member after knitting. Weaving according to a given bar pattern is described, for example, in "Warp Knitting Production" by Dr. S. Raz, Melliand Textilberichte GmbH, Rohrbacher Str. 76, D-6900 Heidelberg, Germany (1987), the contents of which are incorporated by reference herein.

Attachment arms 12 and 13 and or sheaths 14 may also include indicia thereon to signify the correct orientation for implantation into a patient. The indicia may include various markings, colors, apertures, symbols, or combinations thereof. Further, the indicia may be located on the attachment arms, the sheaths, or both. In the embodiment shown in FIGS. 1 and 2, sheaths 14 around attachment arms 12 include indicia 12A to show that attachment arms 12 are the superior attachment arms, and sheaths 14 around attachment arms 13 include indicia 13A to show that attachment arms 13 are the inferior attachment arms.

Apparatus 10 includes dilating connectors 30. Suitable dilating connectors are disclosed in Published U.S. Patent Application Serial Nos. 2002/151762 and 2002/147382 and U.S. patent application Ser. No. 10/386,897, filed Mar. 11, 2003.

Figure 5:
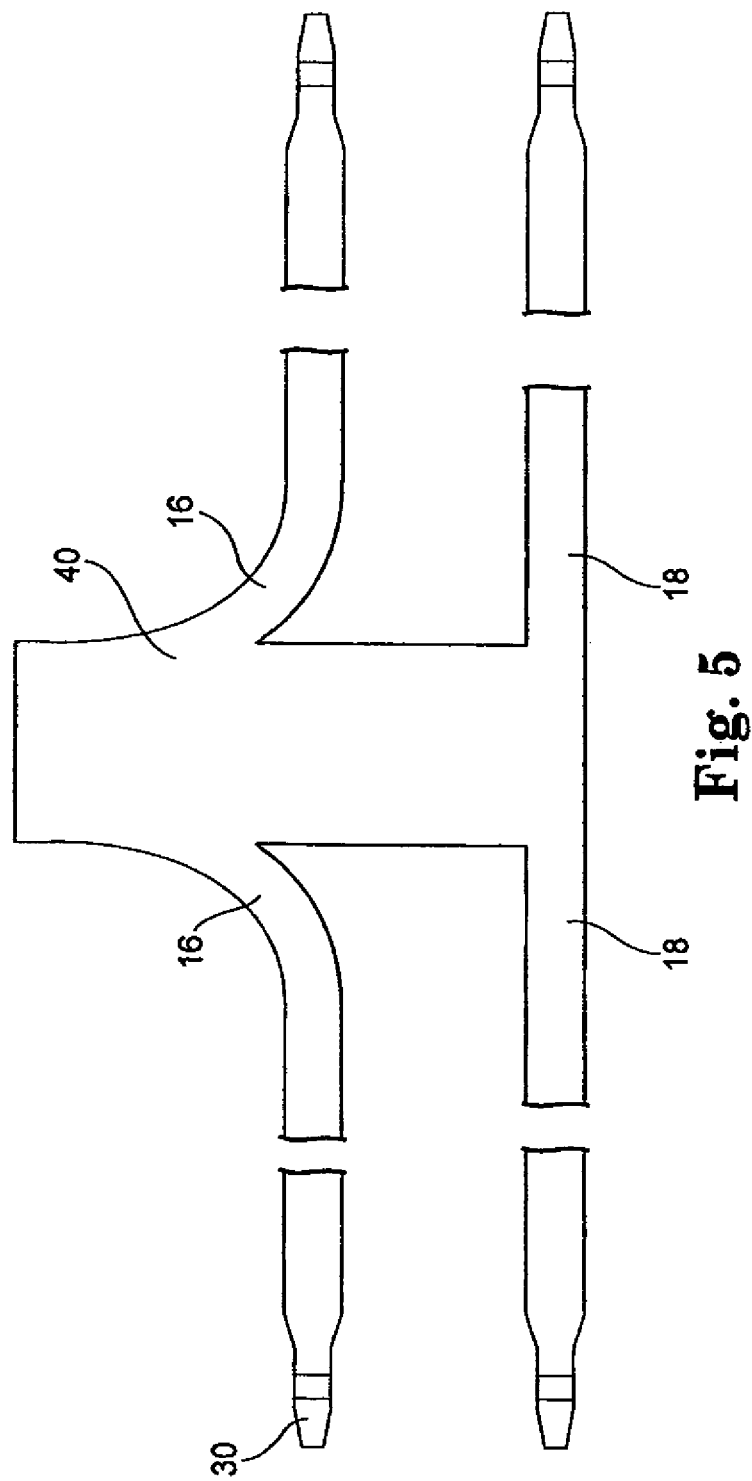
FIG. 5 is a fragmentary top view of the variable attachment arm support apparatus that has been modified in accordance with the present invention.

Before implantation, support member 40 may be trimmed based on patient anatomy to provide a variable attachment arm position. Shape of support member 40 allows the attachment arm positions to be customized to repair a cystocele without lifting a patient's bladder and without placing undue tension on the bladder or vaginal wall. For example, FIG. 1 illustrates a support member configured to maximize the distance between superior arms 16 and the inferior arms 18. Support 40 is cut along lines 20 and 22 to remove section 28. Similarly, support 40 is cut along lines 24 and 26 to remove section 30. This results in the configuration illustrated in FIG. 5. In this configuration, the distance between superior arms 16 and inferior arms 18 can be maximized. Superior arms 16 are flexible to allow for movement to a position substantially parallel to inferior arms 18, or a position substantially skewed to inferior arms 18.

Figure 2:
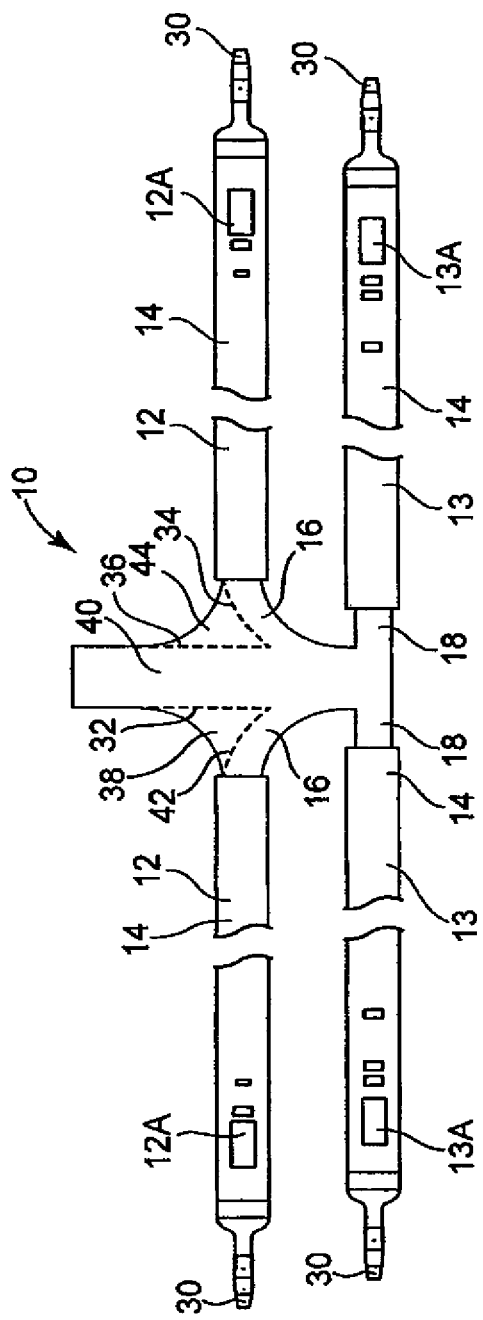
FIG. 2 is a fragmentary top view of an alternative embodiment of the variable attachment arm support apparatus.
Figure 6:
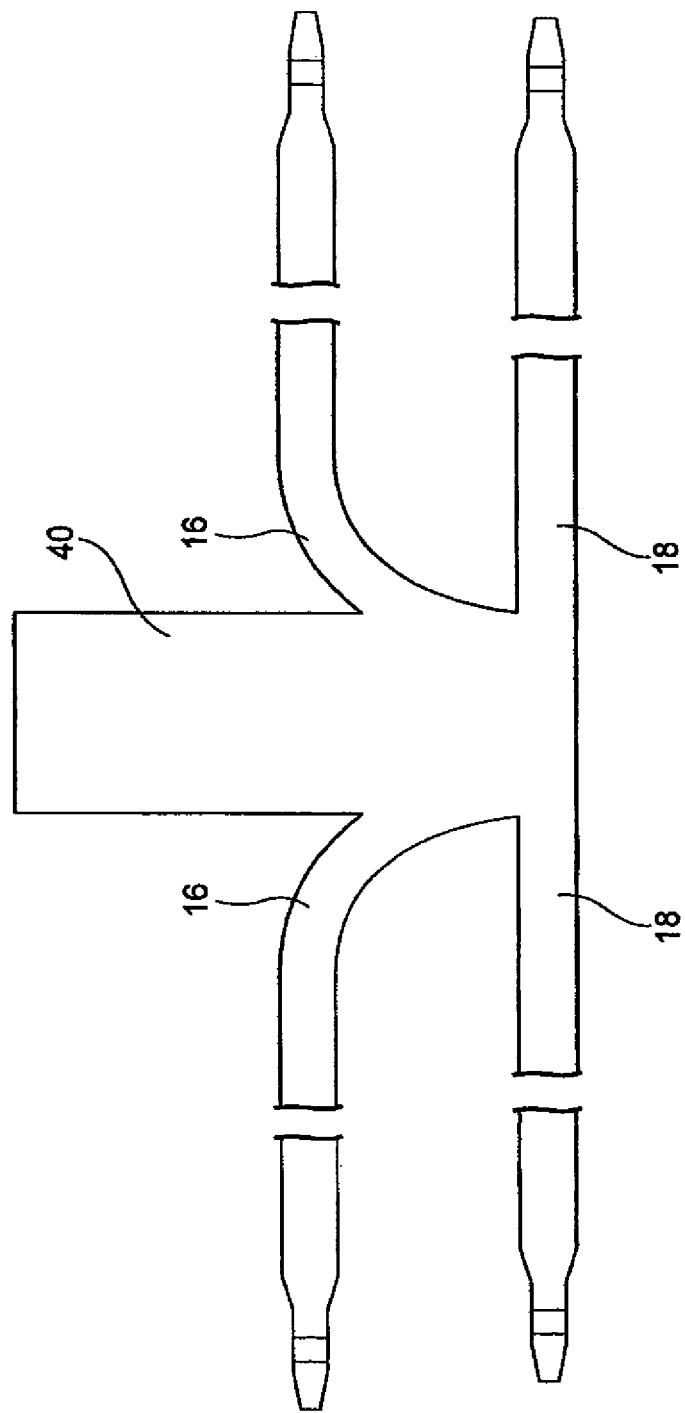
FIG. 6 is a fragmentary top view of the variable attachment arm support apparatus that has been modified in accordance with the present invention.
Figure 7:
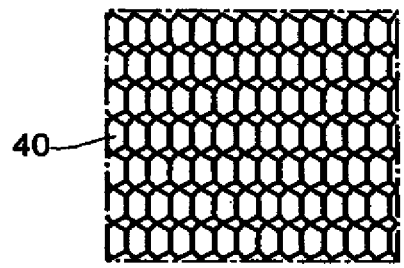
FIG. 7 is a close up view of the weave pattern of an embodiment of the variable attachment arm support apparatus.
Figure 8:
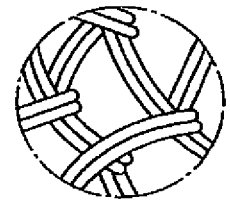
FIG. 8 is a close up view of an alternate weave pattern for the variable attachment arm support apparatus.

An alternative embodiment of the variable attachment surgical support apparatus 10 is shown in FIG. 2. Before implantation, support member 40 can be trimmed to minimize the distance between superior arms 16 and the inferior arms 18. Support 40 is cut along lines 42 and 32 to remove section 38. Similarly, support 40 is cut along lines 34 and 36 to remove section 44. This results in the configuration illustrated in FIG. 6. In this configuration, the distance between superior arms 16 and inferior arms 18 can be reduced. Superior arms 16 are flexible to allow for movement to a position substantially parallel to inferior arms 18, or a position substantially skewed to inferior arms 18.

With reference to FIGS. 3 and 4, an embodiment of a attachment arm for a surgical apparatus is shown. In one embodiment, attachment arm 12 includes tensioning suture 17. Tensioning suture 17 passes through the mesh of attachment arm 12 multiple times, as shown in FIGS. 3 and 4. Tensioning suture 17 is affixed to attachment arm 12 at points 19, to allow transfer of tension from the suture to the attachment arm. In one embodiment, tensioning sutures are included in all the attachment arms 12 and 13 of the support apparatus. Tensioning suture 17 is configured to eliminate slack in a attachment arm that is already surgically implanted in the body. By tightening the attachment arm with suture 17, rather than pulling on the attachment arm itself, the surgeon prevents damage to the attachment arm due to deformation. Damage to surrounding tissues due to excessive movement of the attachment arm during adjustment can also be avoided. Attachment arm 12 also includes a connection point for loosening suture 16. Loosening suture 16 is pulled by the surgeon to loosen the installed support member, if necessary.

Apparatus 10 can be fabricated from a variety of synthetic and non-synthetic material. Suitable non-synthetic materials include allografts, homografts, heterografts, autologous tissues, cadaveric fascia, autodermal grafts, dermal collagen grafts, autofascial heterografts, whole skin grafts, porcine dermal collagen, lyophilized aortic homografts, preserved dural homografts, bovine pericardium and fascia lata. Other examples of suitable materials include those disclosed in published U.S. patent application Ser. No. 200210072694. Specific examples of synthetic materials include, but are not limited to, polypropylene, cellulose, polyvinyl, silicone, polytetrafluoroethylene, polygalactin, Silastic, carbon-fiber, polyethylene, nylon, polyester (e.g. Dacron) polyanhydrides, polycaprolactone, polyglycolic acid, poly-L-Iactic acid, poly-D-L-lactic acid and polyphosphate esters. See Cervigni et al., The Use of Synthetics in the Treatment of Pelvic Organ Prolapse, Current Opinion in Urology (2001), 11: 429-435.

Figure 9:
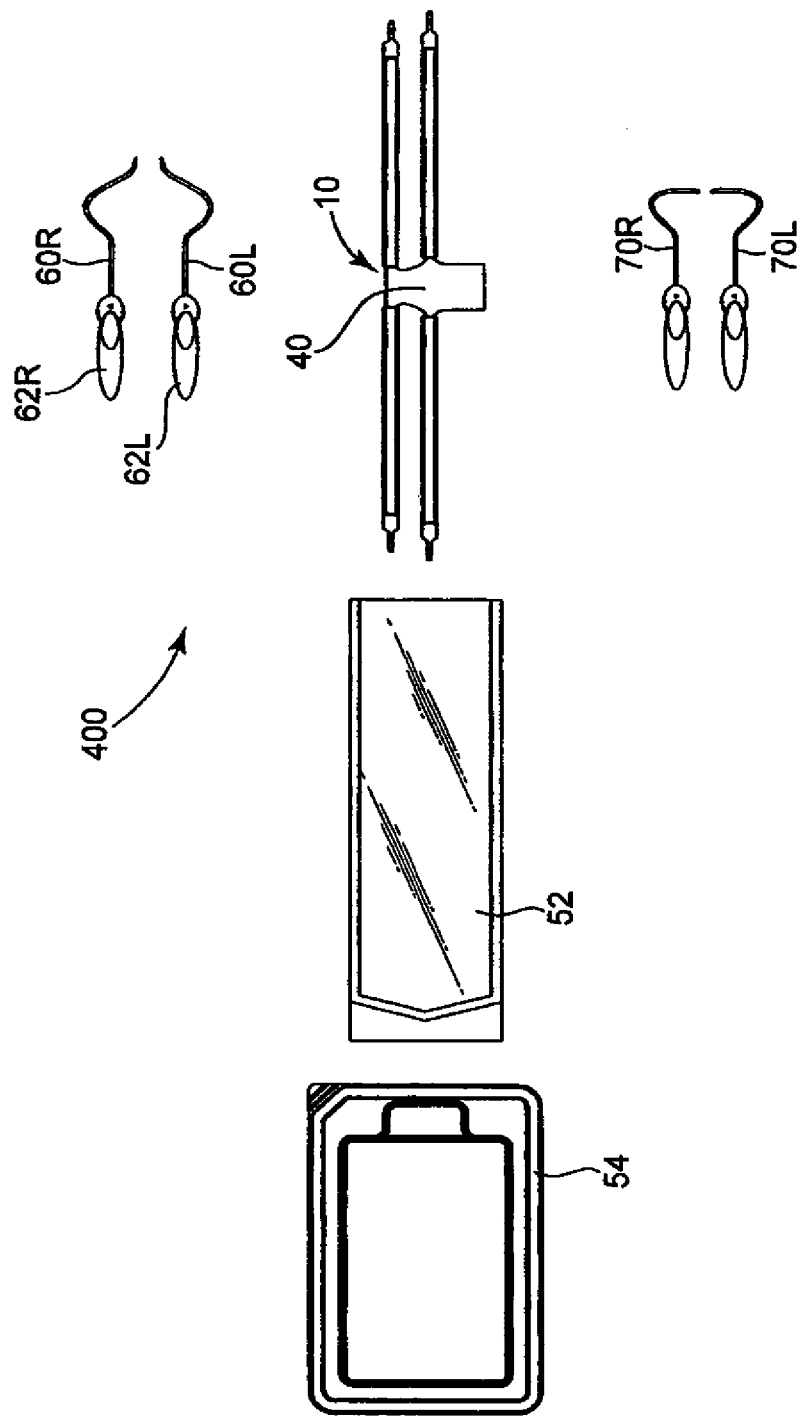
FIG. 9 is a top view of a surgical kit of an embodiment of the present invention.
Figure 10:
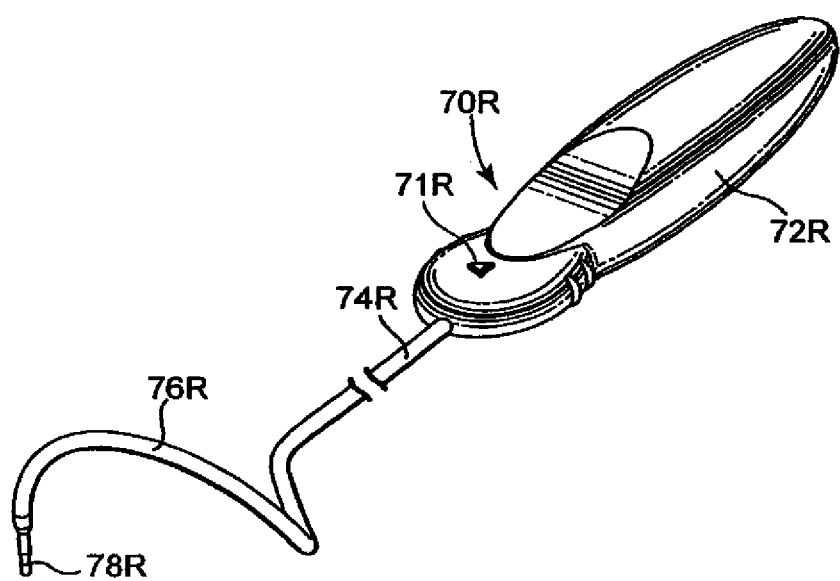
FIG. 10 is a perspective view of an embodiment of a right superior needle (the superior needle held in the surgeon's right hand) of the present invention.
Figure 11:
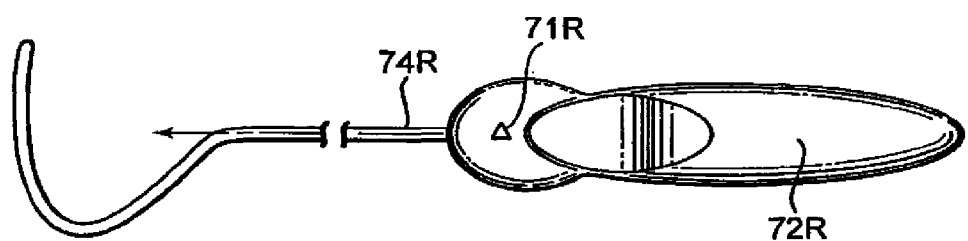
FIG. 11 is a top view of an embodiment of the right superior needle of the present invention.
Figure 12:
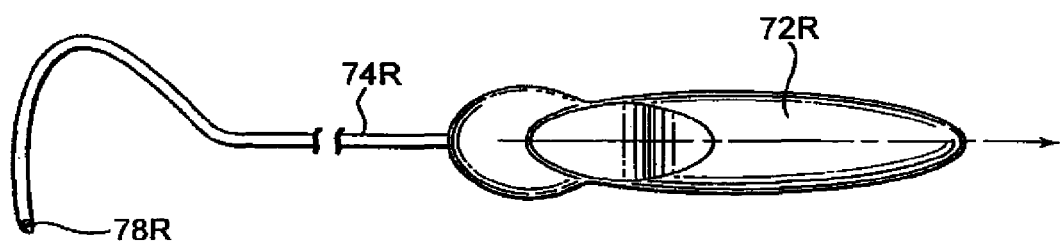
FIG. 12 is a bottom view of an embodiment of the right superior needle of the present invention.
Figure 13:
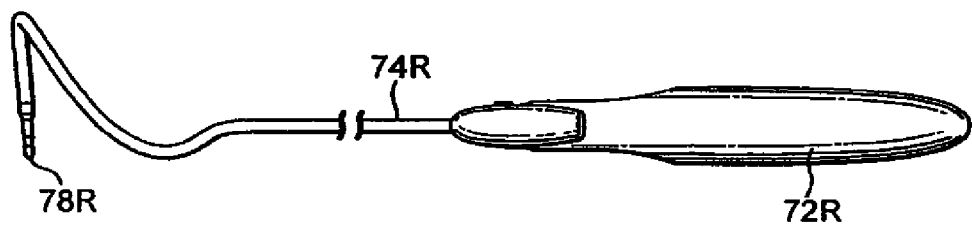
FIG. 13 is a left side view of an embodiment of the right superior needle of the present invention.
Figure 14:
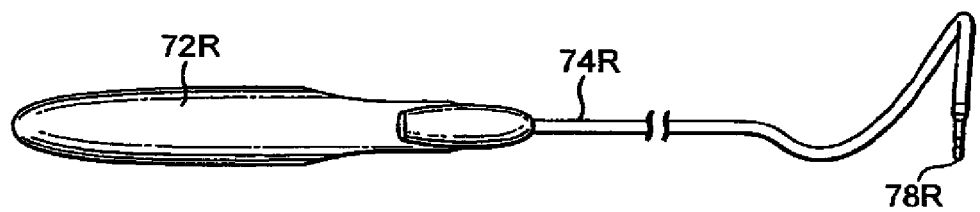
FIG. 14 is a right side view of an embodiment of the right superior needle of the present invention.
Figure 15:
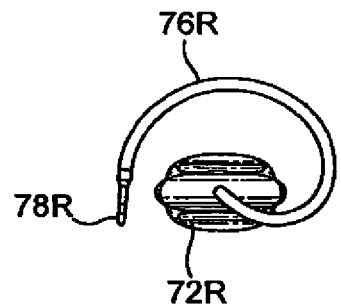
FIG. 15 is a front view of an embodiment of the right superior needle of the present invention.
Figure 16:
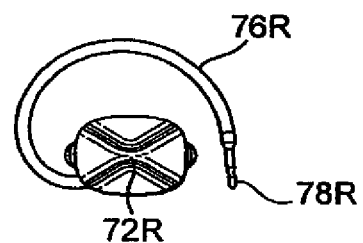
FIG. 16 is a rear view of an embodiment of the right superior needle of the present invention.
Figure 17:
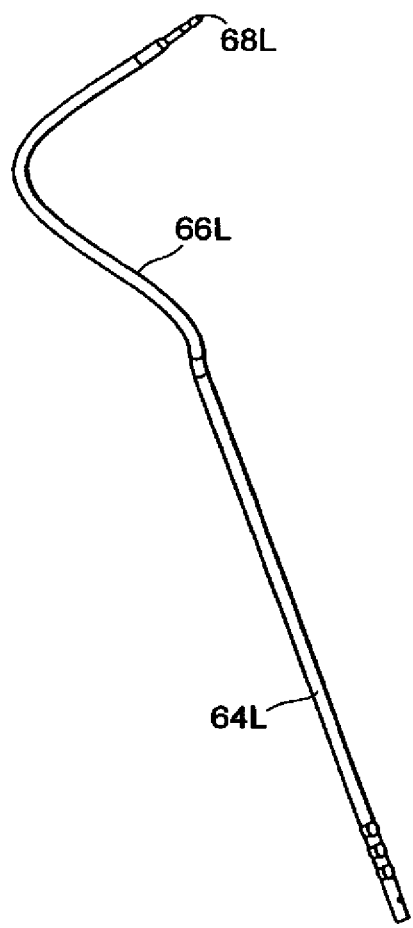
FIG. 17 is a side perspective view of an embodiment of a left inferior needle shaft of the present invention, without a handle.
Figure 18:
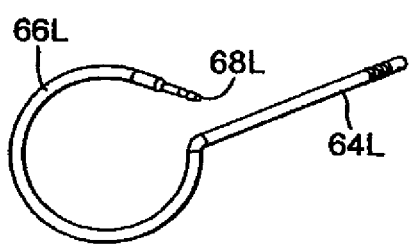
FIG. 18 is a front perspective view of an embodiment of the left inferior needle shaft of the present invention, without a handle.
Figure 22:
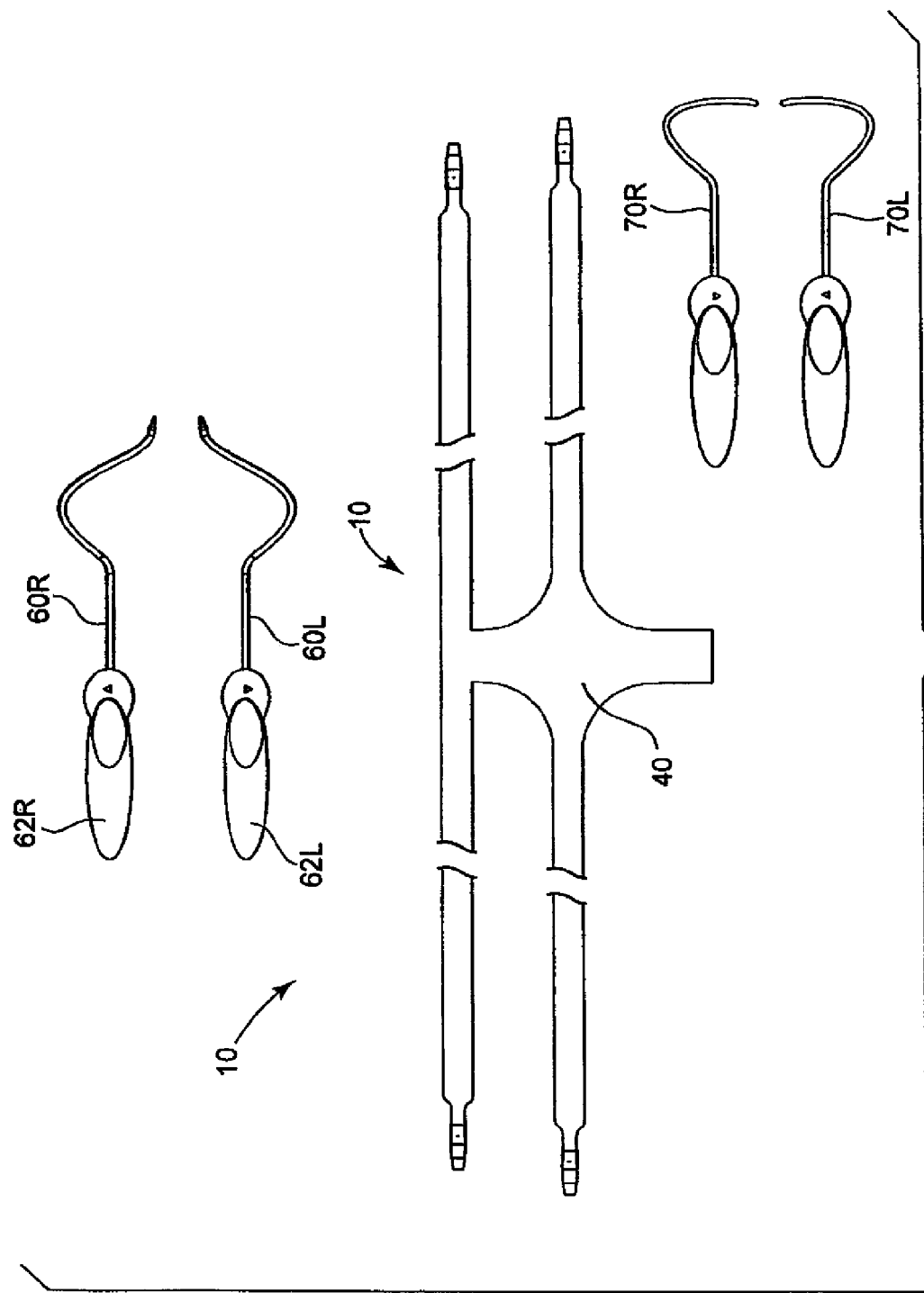
FIG. 22 is a front view of an embodiment of a set of four needles and a support apparatus with four connectors, wherein the connectors are matched to the needles using colors.

With reference to FIG. 9, in another aspect, the present invention includes a surgical kit 400. The kit 400 preferably includes at least two superior needles 70R and 70L. Right superior needle 70R is configured to be held in the surgeon's right hand and such that the tip of the needle enters an incision on the left side of the patient where the left adductor longus tendon of the patient inserts into a left portion of the pubic ramus bone of the patient, lateral to the edge of the pubic ramus bone, and travels through the top of the left obturator foramen to exit through an incision in the vagina of the patient. Left superior needle 70L is configured to be held in the surgeon's left hand and such that the tip of the needle enters an incision on the right side of the patient where the right adductor longus tendon of the patient inserts into a right portion of the pubic ramus bone of the patient, lateral to the edge of the pubic ramus bone, and travels through the top of the right obturator foramen to exit through an incision in the vagina of the patient.

In alternative embodiments of the present invention, the kits may further include the needles described in published U.S. patent application Ser. Nos. 20023-006S246-Al; 2002-0151762-A1; 2002-0147382-A1; 2002-0107430-A1, U.S. patent application Ser. No. 2002-0099258-A1 and U.S. patent application Ser. No. 2002-0099259-A1; and U.S. Provisional Application Ser. Nos. 60/263,472, filed Jan. 23, 2001; 60/269,829, filed Feb. 20, 2001; 60/281,350, filed Apr. 4, 2001; 60/295,068, filed Jun. 1, 2001; 60/306,915, filed Jul. 20, 2001, and 60/332,330, filed Nov. 20, 2001. In an embodiment that is particularly suitable for a. transobturator surgical procedure, the needles include needles as described in U.S. patent application Ser. No. 10/306,179 filed Nov. 27, 2002.

Various elements of the kits of the present invention may be packaged together as shown in FIG. 9 with a cover 52 and tray 54. Alternatively, the individual elements may be separately packaged or packaged in subassemblies depending on a variety of factors such as shelf life and sterilization requirements. They may be assembled at the manufacturing location or at the healthcare location. Any suitable sterilization procedure may be utilized to sterilize the contents of a kit. Suitable sterilization techniques include, but are not limited to, steam, ethylene oxide, electron beam, vapor (e.g. hydrogen peroxide or peracetic acid), gamma or plasma procedures.

The kit shown in FIG. 9 includes a support apparatus including a mesh support member 40. It should be readily apparent to one skilled in the art that kits using biological support members, as described above, may be made, and these modifications are within the scope of the invention as claimed. Further, a kit comprising a biologic graft may have the biologic graft pre-attached to the attachment arms, or the graft may be separate from the attachment arms and require the surgeon to attach the attachment arms to the graft, as discussed below. The kit shown in FIG. 9 also includes four needles: right inferior needle 60R, left inferior needle 60L, right superior needle 70R, and left superior needle 70L. Embodiments of these needles are shown in FIGS. 10-21 and are described herebelow.

FIGS. 10-16 illustrate an embodiment of right superior needle 70R of the present invention. (Left superior needle 70L is a mirror image of the right superior needle 70R.) Right superior needle 70R includes indicia 71R, handle 72R, shaft 74R, curved portion 76R, and tip portion 78R. Indicia 71R designates whether the needle is the right or left needle by pointing to the surgeon's right or left side, as the surgeon holds the needle handle. (The surgeon's right side corresponds to the patient's left side.)

Figure 31:
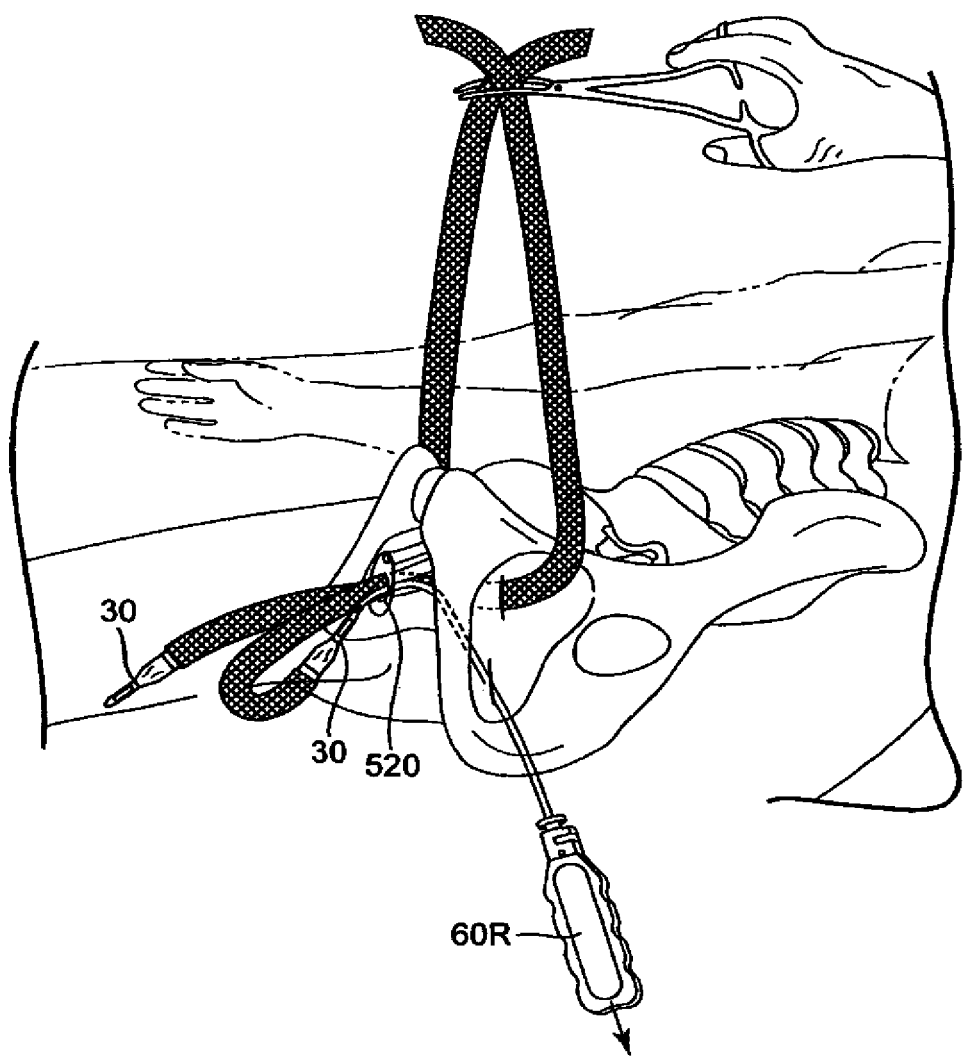
FIG. 31 is a perspective view of a right inferior needle tip exiting the vaginal incision.

An exemplary shaft of left inferior needle 60L without handle 62L is illustrated in FIGS. 17-21. (Right inferior needle 60R is a mirror image of the left inferior needle 60L.) Left inferior needle 60L includes a handle 62L, a shaft 64L, a curved portion 66L, and a tip portion 68L. Left inferior needle 60L is configured to be held in a surgeon's left hand such that tip 68L enters an incision 530L on the right side of the patient where a right inferior edge of the pubic ramus bone of the patient ends at a bottom of the right obturator foramen of the patient, and travels through the right obturator foramen to exit through an incision in the vagina of the patient. Right inferior needle 60R is configured to be held in a surgeon's right hand such that tip 68R enters an incision on the left side of the patient where a left inferior edge of the pubic ramus bone of the patient ends at a bottom of the left obturator foramen of the patient, and travels through the left obturator foramen to exit through an incision in the vagina of the patient. This is shown in FIG. 31. The above-described needles may be disposable or reusable.

Figure 23:
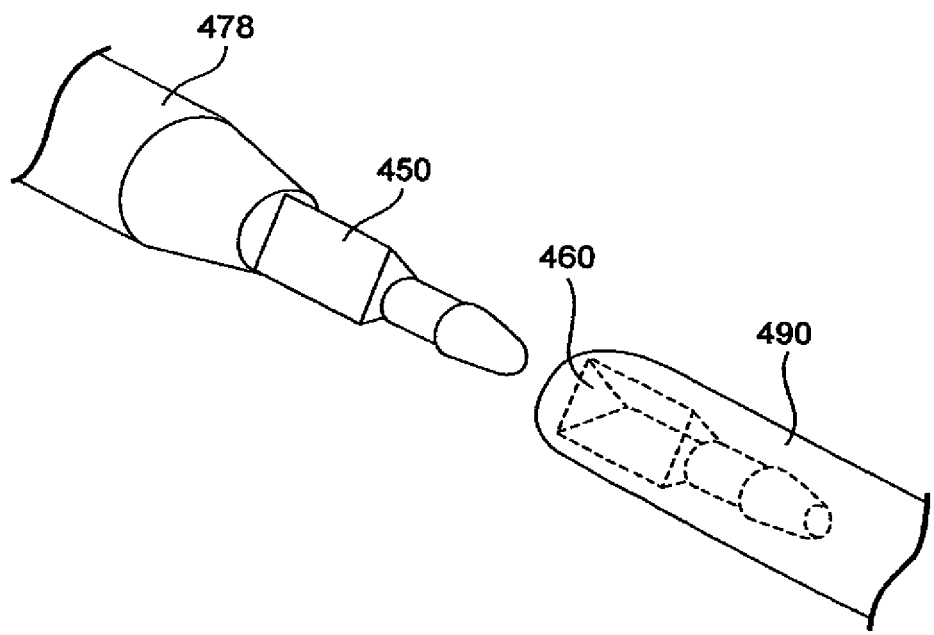
FIG. 23 is a perspective view of a first needle tip and removable connector of an embodiment of the present invention.
Figure 24:
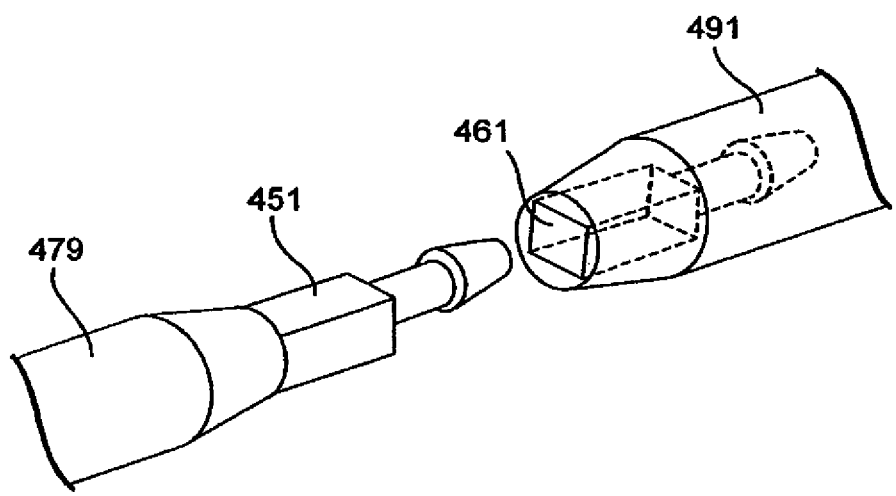
FIG. 24 is a perspective view of a second needle tip and removable connector of an embodiment of the present invention.
Figure 25:
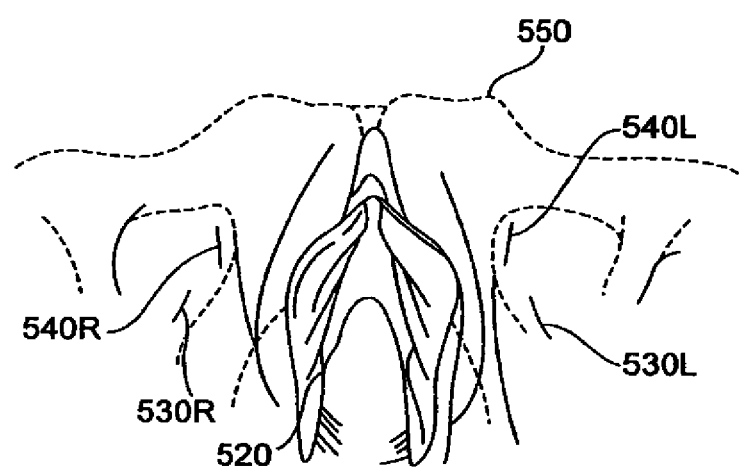
FIG. 25 is a front view of a patient showing the four needle entry incisions.
Figure 26:
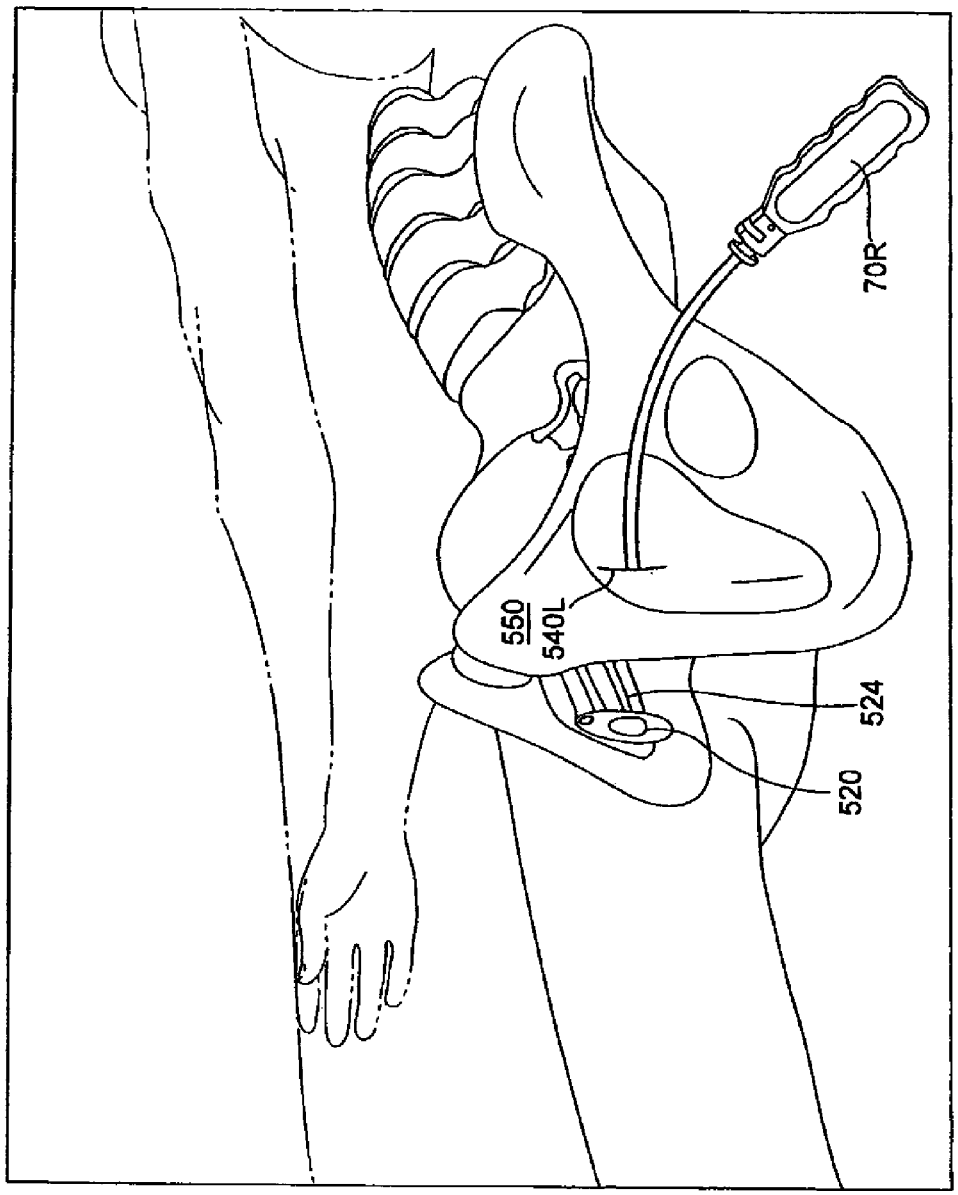
FIG. 26 is a perspective view of a right superior needle tip entering the left superior incision (the superior incision on the patient's left side)
Figure 27:
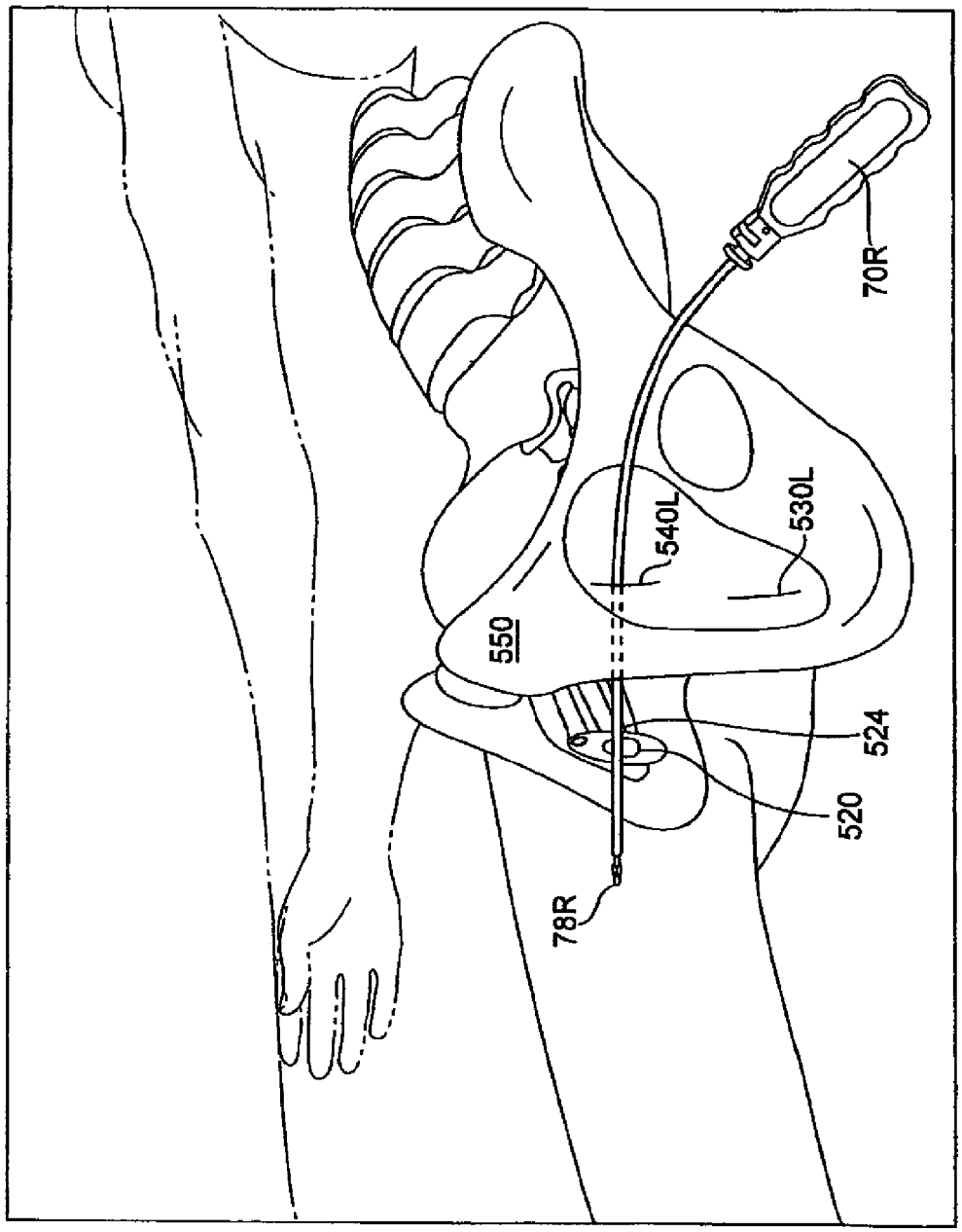
FIG. 27 is a perspective view of a right superior needle tip exiting the vaginal incision.
Figure 28:
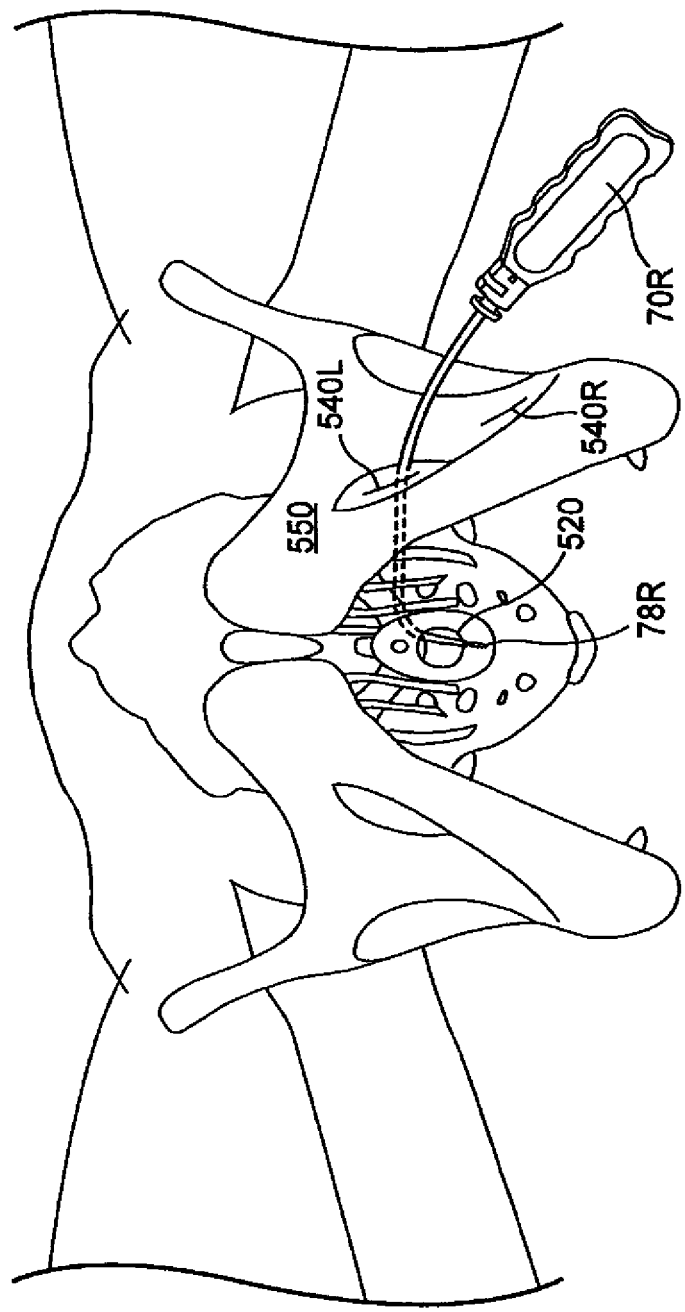
FIG. 28 is a front view of a right superior needle tip exiting the vaginal incision.
Figure 29:
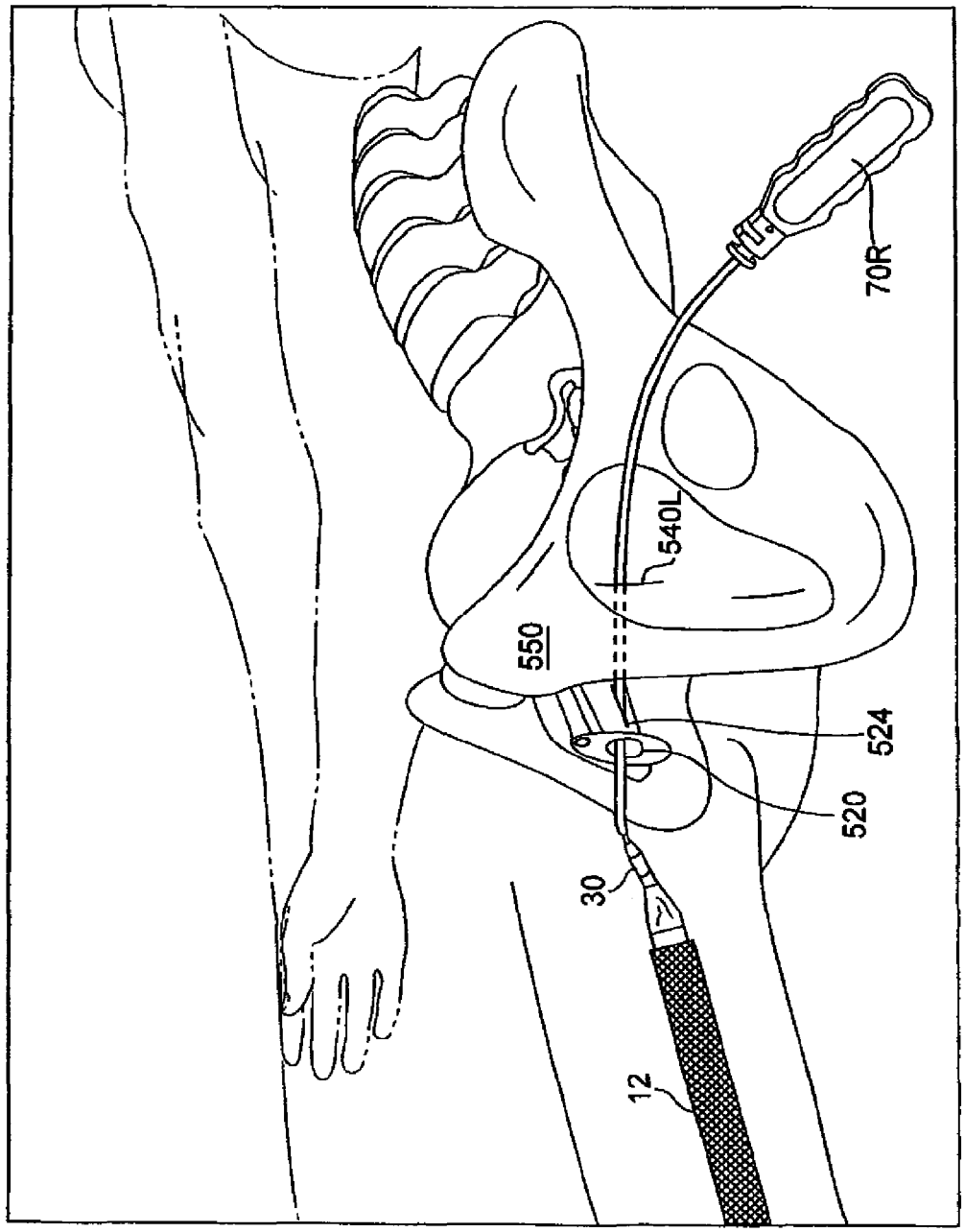
FIG. 29 is a perspective view of a right superior needle tip connected to the right superior connector (the superior connector on the surgeon's right side)
Figure 30:
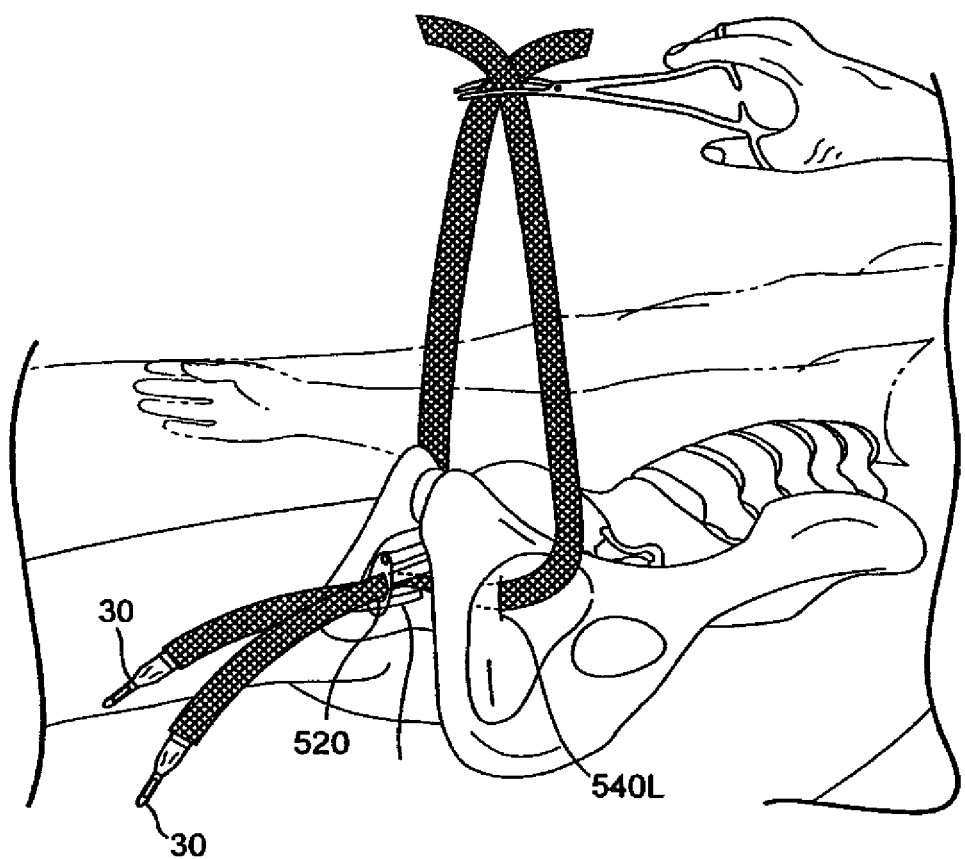
FIG. 30 is a perspective view of the superior attachment arms and the support member in place and the inferior attachment arms extending outside the vaginal incision.

FIGS. 23 and 24 are perspective views of a needle tips having a cross sections that are configured to match the cross sections of a connector aperture. FIG. 23 shows that the cross section of portion 450 of needle tip portion 478 is a triangle. The cross section of portion 450 matches triangle shaped aperture 460 in connector 490. FIG. 24 shows that the cross section of portion 451 of needle tip portion 479 is a square. The cross section of portion 451 matches square shaped aperture 461 in connector 491.

In one embodiment each needle tip has a cross section that matches the cross section of an aperture of the corresponding connector, and the tip cross section is incompatible with the other connector apertures. For example, the cross section of the portion 450, a triangle, would not fit in aperture 461, a square, and vice versa. Thus, even if the connectors are confused, it is physically impossible for a surgeon to insert the needle tip in the incorrect connector without damaging the tip or connector. Other shaped tips and apertures are possible while remaining within the scope of the invention.

FIGS. 25-32 illustrate an exemplary method for using the disclosed surgical support apparatus 10 having a mesh support member 40. In preparation for surgery, the patient is placed in a modified dorsal lithotomic position with hips flexed, legs elevated in stirrups and buttocks even with edge of the surgical table. The patient's bladder is emptied. A catheter is not required during the procedure, but may aid in identifying the urethra during the procedure. A weighted vaginal retractor or other suitable vaginal retraction may also be used.

Next, it is necessary to mark the length of the vaginal incision with a skin pencil starting below the bladder neck, over the most prominent part of the prolapse, to the lowermost part of the prolapse. (Variations may occur in specific incisions due to individual technique and patient anatomy.) An incision is made over this marking. The incision site may be infiltrated with saline, if desired. An Allis forceps is placed on the incision margin to expose the incision. The patient's bladder is dissected off the vagina up to the lateral sulcus and posterior to the vaginal vault. This dissection allows palpation of the medial edge of the inferior pubic ramus, assisting in guiding the superior and inferior needles to the exit points free from the bladder. The patient's cystocele may then be reduced using midline plication.

Markings are then made to identify the locations for needle entry incisions. The vaginal dissection is completed prior to marking needle entry incisions to allow for digital palpation along the ischiopubic ramus. The needle entry points are palpated internally and externally with the thumb and index finger before marking, as discussed hereafter.

Next, the edge of the ischiopubic ramus is palpated beginning at the level of the vaginal incision, continuing along the edge of the bone cephalad toward the level of the clitoris denoting where the adductor longus tendon inserts into the pubic ramus. The superior skin incisions are marked approximately at this location and lateral to the edge of the bone. The markings are made according to the same method on both sides (right and left) of the patient's body. Both marks lie in a straight line at the approximate level of the clitoris. The edge of the inferior pubic ramus is palpated until it ends at the bottom of the obturator foramen. The inferior skin incisions are then marked. The inferior skin incisions are located at a point approximately 3 centimeters below and 2 centimeters lateral to the superior marks. Again, the markings are made according to the same method on both sides of the patient's body.

A small vertical stab incision is made over all four markings to provide needle entry incisions. Right superior incision 540R, left superior incision 540L, right inferior incision 530R, and left inferior incision 530L are all shown in FIG. 25. (Right and left with regard to the incisions are the patient's right and left sides.)

The surgical kit described with reference to FIG. 9 is opened. The package integrity is checked to ensure that the kit was not compromised in shipping, and the components of the kit are inspected for damage.

The following method describes the attachment arms on the surgeon's right side (the patient's left side) being surgically installed before the attachment arms on the surgeon's left side (the patient's right side). However, it should be readily apparent to one skilled in the art that the attachment arms of either side could be installed first, and this modification is within the scope of the invention as claimed.

Figure 33:
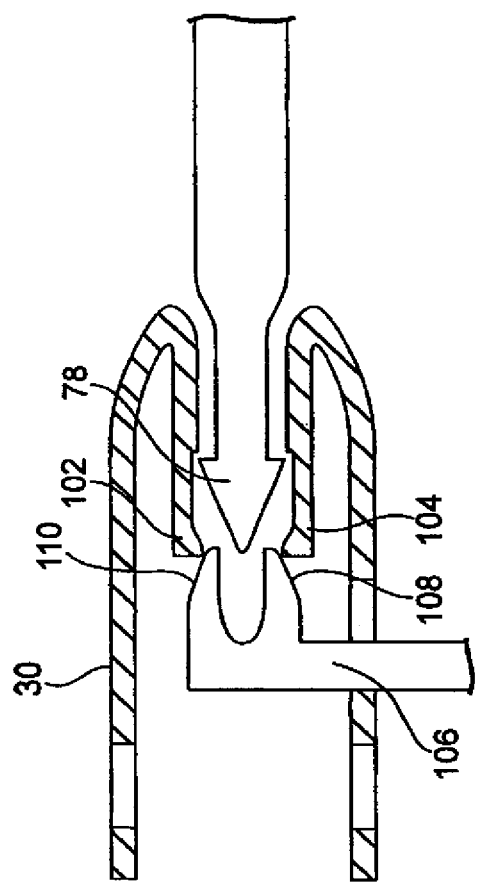
FIG. 33 is a top cross-sectional view of a removal tool disengaging a connector from a needle tip during a first phase.

Tip 78R of right superior needle 70R is then inserted through left superior incision 540L, through the left obturator foramen, and then through the vaginal incision 524. Tip of right superior needle 70R is pointed perpendicular to the skin with tip 78R in the left superior incision 540L, shown in FIG. 33. The thumb from the surgeon's right hand is on the outside curve of needle to control the needle movement as it perforates the obturator membrane and muscle. The right thumb pushes the needle through the obturator muscle and membrane. The needle shaft and handle is positioned at a 45° angle to the patient's vertical axis and close to the patient's body. The needle handle is rotated to move the needle tip and curve around the posterior surface of the ischial pubic ramus toward the vaginal incision and index finger. (If the needle tip hits the pubic bone during rotation, the needle is retracted. The needle tip is then penetrated beyond initial insertion depth and rotate again toward the vaginal incision.) The needle tip is palpated with the surgeon's finger. The finger meets the needle tip as it moves around the pubic ramus. (If the needle tip cannot be located, the needle tip is retracted to just behind the pubic ramus and advanced again.) The needle tip is guided by the surgeon with the surgeon's finger towards the vaginal incision until the needle tip extends through the vaginal incision, shown in FIGS. 27 and 28.

The support member is then oriented so that the tail of the graft points away from the surgeon. The right superior connector is connected to the tip of the right superior needle, the tip extending out of the vaginal incision, as shown in FIG. 36. The superior needle connectors are closest to the leading edge of the graft that will be below the bladder neck.

Before attaching the connectors, the surgeon ensures that the self-fixating mesh and graft are not twisted. However, the connectors are removable once snapped onto the needle. This feature of the invention enables the physician to make adjustments to support member 40 as needed. For example, a surgeon may wish to remove area 28 and area 30 of support member 40 to increase the distance between superior arms 16 and inferior arms 18. Alternatively, a surgeon may wish to remove area 38 and area 44 of support member 40 to decrease the distance between superior arms 16 and inferior arms 18.

The connector 30 is attached to the needle 78 and the needle is rotated back through the skin incision pulling the connector and associated insertion sheath and graft into position. The process is then repeated with the left needle on the patient's right side.

During the procedure, it may be desirable to remove the connector 30 from the needle 78. This process will be discussed with reference to FIGS. 33 and 34. Connector 30 includes deflector tabs 102 and 104. Needle 78 is inserted into connector 30 and locked in place between tabs 102 and 104. To retract needle 78 from connector, removal tool 106 is used. Removal tool 106 includes a first inclined surface 108 and a second inclined surface 110. As tool 106 is moved toward needle 78, surface 110 contacts tab 102 and surface 108 contacts tab 104. As tool is moved closer toward needle 78, tab 102 moves away from tab 104 as shown in FIG. 34. This configuration allows for deflection of the connector 30 to enable the needle 78 to separate from connector. Tool 106 can be disposed into connector 30 through aperture 112. Tool can be removed from aperture, or slidably fastened thereto while remaining within the scope of the invention. It shall be understood that removal tool 106 can comprise a variety of configurations while remaining within the scope of the invention.

The partially implanted apparatus is shown in FIG. 37, with superior attachment arms and support member 40 implanted and the inferior attachment arms extending outside the body through the vaginal incision. The insertion sheaths and mesh are then cut below the indicia on the end portion of the plastic sheath and discarded. This step allows the sheath to slide freely relative to the mesh. The sheaths are not removed at this time.

Next, the tip of the right inferior needle is inserted through left inferior incision 530L, through the left obturator foramen, and then through the vaginal incision. The tip of the right inferior needle is pointed perpendicular to the skin with the tip in the left inferior incision. The exit point for the needle is confirmed to be clear of the bladder wall by the surgeon placing their right index finger at the distal end of the vaginal incision and visualizing where needle exits the distal end of vaginal incision. The surgeon's right thumb is on the outside curve of needle to control the needle movement as it perforates the obturator membrane and muscle. The right thumb pushes the needle through the obturator muscle and membrane.

The needle shaft and handle is positioned parallel to the patient's vertical axis and close to the patient's body. The needle handle is rotated, moving the needle tip and curve toward the distal end of the vaginal incision. The surgeon must use care during this step to prevent bleeding. The needle tip is then palpated as it moves through the distal end of the vaginal incision. The right inferior needle tip is shown extending outside the vaginal incision in FIG. 31.

The right inferior connector is connected to the right inferior needle tip. Again, before attaching the connectors, the surgeon ensures that the self-fixating mesh and graft are not twisted. However, the connectors are removable once snapped onto the needle. The needle is rotated back through the skin incision pulling the connector and associated plastic insertion sheath and graft into position. The above process is repeated with the left inferior needle on the patient's right side.

The insertion sheath and mesh are then cut below the indicia on the end portion of the plastic sheath and discarded. This step allows the sheath to slide freely relative to the mesh. The sheaths are not removed at this time.

Next, it is desirable to perform a cystoscopy to check the integrity of the uterus and bladder. Any vaginal retraction is then removed to allow adjusting the tension of the mesh to reduce bladder bulge. The surgeon confirms the mesh is lying flat and not overlapping under the vaginal wall. The superior leading edge of the support member should be positioned below the bladder neck without tension. The inferior tail portion of the support member should is positioned at the distal end of the vaginal incision or towards the vaginal apex without tension.

If the mesh needs to be loosened, an instrument may be placed between the mesh and vaginal wall and pulled down, or away from the vaginal wall until proper tension is achieved. Each of the four plastic sheaths are removed and discarded, while ensuring the support member graft is not over tensioned. Once the plastic sheaths are removed, further adjustment is minimized.

If the mesh requires tightening, the tensioning suture exiting the skin incision on each side is grasped using a hemostat. The suture is wrapped around the hemostat to improve the grip and pulled up or out to tighten until proper tension is achieved. To loosen a biologic graft, the surgeon uses a hemostat or a clamp to pull from each of the hanging loosening sutures. The surgeon uses the clamps to pull down and loosen the attachment arm mesh as desired. The surgeon should exercise caution to avoid pulling on tab 18 on loosening suture 16 to loosen the attachment arm mesh.

Figure 32:
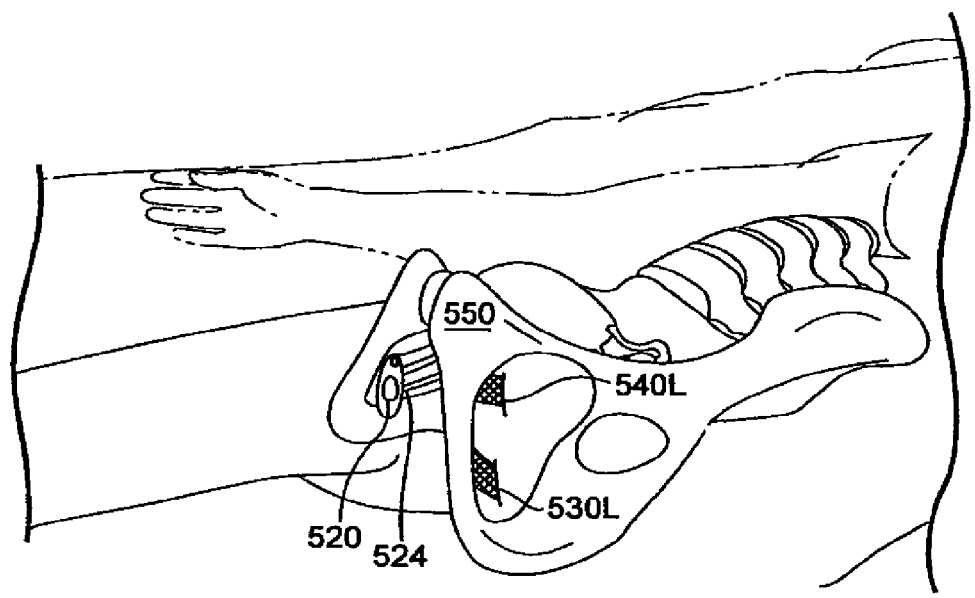
FIG. 32 is a perspective view of all the attachment arms and the support member in place and the sheaths removed.

Next, the surgeon cuts one end of each loosening suture and pulls tab 18 until the entire loosening suture is removed. The mesh is then trimmed at the level of the subcutaneous tissue and all five incisions are closed. Excess vaginal tissue may be excised. Variations of this step may occur due to individual technique and patient anatomy. The final implanted apparatus is shown in FIG. 32.

After the operation, a catheter and/or vaginal pack can be used at the discretion of the surgeon, but should be removed prior to discharge. During this time, antibiotic prophylaxis should be given. The ability of the patient to empty the bladder should be confirmed prior to discharge.

If a biologic graft is used, the following steps are performed before making the vaginal incision. The biologic graft is removed from the package and prepared per included instructions, if needed. A precut biologic is prepared by orienting the graft with the tail portion pointing at the surgeon. The graft material is inserted into the open clamp using printed marks as guides to center the graft. (The printed side of the plastic sheath is facing the surgeon as the surgical apparatus is placed in the body.) The clamp is released to secure graft material. A desired suture is passed up through the clamp using a suturing mark as a guide. The suture is then passed down using the opposite suturing mark as the guide. The passed sutures are then secured using the surgeon's knot(s) of choice. Additional throws are made if needed. The clamp sutures are cut by passing a scissors or a scalpel down the scissors slot on each side of the clamp. The clamps are then removed. The clamp attachment sutures remain with the clamp. The surgeon assesses the attachment of the graft material mesh tape. The protective sheath is slid over the mesh connection to aid deployment.

The preceding steps are repeated on the opposite side of the graft. The sutures are passed such that the attachment knots are all on the same side of the graft. The biologic is placed in a saline bath to keep it hydrated during the remainder of the procedure. The graft tail is trimmed at the time of vaginal marking and dissection to reflect patients anatomy, if needed.

In addition, when using the biologic graft, the surgeon should exercise care when drawing the attachment arm through the body so that the sheath covers the graft connections and that the graft material and graft connections are not damaged.

All patents, patent applications, and publications cited herein are hereby incorporated by reference in their entirety as if individually incorporated. Various modifications and variations of the present invention are possible in view of the above teachings. It is therefore to be understood that the drawings and descriptions herein are offered by way of example to facilitate comprehension of the invention and should not be construed to limit the scope thereof.

What is claimed is:

1. A kit for repairing cystocele comprising:
   an adjustable support apparatus comprising:
      a support member comprising an upper edge, a lower edge, and first and second sides extending between the upper and lower edges;
      first and second superior attachment arms, each of which comprises an upper edge, a lower edge, and a longitudinal axis extending along its length, wherein the first superior attachment arm extends from the first side of the support member and the second superior attachment arm extends from the second side of the support member; and
      first and second inferior attachment arms, each of which comprises and upper edge and a longitudinal axis extending along its length, wherein the upper edge of the first inferior attachment arm is spaced from lower edge of the first superior attachment arm and extends from the first side of the support member, and wherein the upper edge of the second inferior attachment arm is spaced from the lower edge of the second superior attachment arm and extends from the second side of the support member,
      wherein each of said attachment arms comprises a connector configured to removably mate with a tip of a needle,
      wherein the longitudinal axis of each of the inferior attachment arms is parallel to the longitudinal axis of each of the superior attachment arms, and
      wherein the upper edge of the support member extends beyond the upper edge of the first and second superior support arms;
   a first needle configured to extend from an incision on a right side of a patient where a right adductor longus tendon of said patient inserts into a right portion of a pubic ramus bone of said patient, lateral to an edge of said pubic ramus bone, through a right obturator foramen of said patient, to an incision in a vagina of said patient; and
   a second needle configured to extend from an incision on a left side of said patient where a left adductor longus tendon of said patient inserts into a left portion of said pubic ramus bone of said patient, lateral to an edge of said pubic ramus bone, through a left obturator foramen of said patient, to said incision in said vagina of said patient.

2. The kit recited in claim 1 wherein said adjustable support apparatus comprises a biologic graft.

3. The kit recited in claim 1 wherein said biologic graft is pre-attached to said at least one of said of attachment arms.

4. The kit recited in claim 1 wherein said adjustable support apparatus comprises a biologic graft fixed over a knitted support member.

5. The kit recited in claim 1 wherein the distance between the superior attachment arms and the inferior attachment arms can be reduced by removing material from the adjustable support apparatus.

6. The kit recited in claim 1, wherein the distance between the superior attachment arms and the inferior attachment arms can be increased by removing material from the adjustable support apparatus.

7. The kit recited in claim 1 wherein the adjustable support apparatus comprises:
   a support member knitted with a first bar setting; and
   a plurality of attachment arms continuously knitted with said support member, the plurality of attachment arms knitted with a second bar setting.

\* \* \* \* \*